US012721542B2

(12) United States Patent
Schinis et al.

(10) Patent No.: US 12,721,542 B2
(45) Date of Patent: Sep. 1, 2026

(54) APPARATUS AND METHOD FOR MEASURING END TIDAL CARBON DIOXIDE ($ETCO_2$)

(71) Applicants: Michael Schinis, Boston, MA (US); Jason Schinis, Boston, MA (US)

(72) Inventors: Michael Schinis, Boston, MA (US); Jason Schinis, Boston, MA (US)

( * ) Notice: Subject to any disclaimer, the term of this patent is extended or adjusted under 35 U.S.C. 154(b) by 497 days.

(21) Appl. No.: 18/137,246

(22) Filed: Apr. 20, 2023

(65) Prior Publication Data

US 2023/0371844 A1 Nov. 23, 2023

Related U.S. Application Data

(60) Provisional application No. 63/332,913, filed on Apr. 20, 2022.

(51) Int. Cl.
*A61B 5/083* (2006.01)
*A61B 5/097* (2006.01)

(52) U.S. Cl.
CPC ........... *A61B 5/0836* (2013.01); *A61B 5/097* (2013.01); *A61B 2503/045* (2013.01)

(58) Field of Classification Search
None
See application file for complete search history.

(56) References Cited

U.S. PATENT DOCUMENTS

| | | | | |
|---|---|---|---|---|
| 2016/0143561 | A1* | 5/2016 | Egan | A61B 5/097 600/532 |
| 2017/0007795 | A1* | 1/2017 | Pedro | A61B 5/082 |
| 2022/0323738 | A1* | 10/2022 | Wainer | A61M 25/0097 |

* cited by examiner

*Primary Examiner* — Jay B Shah
(74) *Attorney, Agent, or Firm* — Pandiscio & Pandiscio

(57) ABSTRACT

Apparatus for passing exhaled gasses from a mouth of a patient to a gas analyzer, the apparatus comprising: a pacifier comprising a distal end, a proximal end and an opening extending from the distal end to the proximal end, wherein the distal end comprises a nipple configured to be inserted into the mouth of the patient and the proximal end comprises a base configured to be positioned against the mouth of the patient; and a connector for connecting the pacifier to the gas analyzer.

8 Claims, 17 Drawing Sheets

APPARATUS AND METHOD FOR MEASURING END TIDAL CARBON DIOXIDE ($ETCO_2$)

REFERENCE TO PENDING PRIOR PATENT APPLICATION

This patent application claims benefit of prior U.S. Provisional Patent Application Ser. No. 63/332,913, filed Apr. 20, 2022 by Michael Schinis et al. for END TIDAL CO2 PACIFIER.

The above-identified patent application is hereby incorporated herein by reference.

FIELD OF THE INVENTION

This invention relates to medical apparatus and methods in general, and more particularly to medical apparatus and methods for measuring end tidal carbon dioxide ($ETCO_2$).

BACKGROUND OF THE INVENTION

End tidal $CO_2$ ($ETCO_2$) is a measurement used to determine how well (i.e., how efficiently) patients are participating in gas exchange during a wide variety of medical procedures. As the human body goes through its normal metabolic processes, carbon dioxide ($CO_2$) is generated as a waste byproduct which must be expelled from the body. One way this is achieved is through gas exchange carried out in the lungs. Circulating blood picks up waste $CO_2$ and carries it to the lungs where it is exchanged for oxygen from inhaled ambient air brought into the lungs via respiration. The now $CO_2$-rich air (i.e., the air remaining in the lungs after oxygen has been exchanged for $CO_2$) is then exhaled, removing the $CO_2$ waste product from the lungs (and hence from the patient). $ETCO_2$ is the measurement of the concentration of $CO_2$ in the patient's exhalations, which measurement is used to gauge how well (i.e., how efficiently) a patient's circulation and gas exchange system is performing. A low $ETCO_2$ level indicates poor circulation and that the patient is not receiving enough oxygen. This can be an early, life-saving indicator for medical professionals to intervene. For this reason, $ETCO_2$ is one of the most important vital signs that clinicians monitor during medical procedures.

Whenever a patient is put under anesthesia, regardless of anesthetic technique used (e.g., general anesthesia, deep sedation, etc.), $ETCO_2$ is monitored closely throughout the procedure. Tubing having luer locks on both ends is attached to the anesthesia circuit on one end (which interfaces with the patient's lung) and to the anesthesia machine on the other end during general anesthesia. As the patient exhales, the tubing carries gases of respiratory exchange from the lung of the patient to an analyzer that determines the percentage of anesthetic gases, oxygen, and carbon dioxide present, as well as other important indicators. During deep sedation cases, one end of the tubing used for this analysis is placed under the patient's facemask and close to their mouth and nose so that the tubing can pick up the patient's exhaled breath (whereby to calculate $ETCO_2$ in the manner discussed above).

If a patient's airway is obstructed, it is not possible to accurately calculate end tidal $CO_2$. Obstruction of the patient's airway commonly occurs when a patient's tongue falls to the roof of their mouths during surgical procedures where the patient is under deep sedation without a protected airway, e.g., where an endotracheal tube (ETT) or laryngeal mask airway (LMA) is not utilized. Therefore, during surgical procedures where the patient is under deep sedation, it is common to insert an object (e.g., an oral airway, a nasal airway, etc.) into the patient's airway in order to ensure that the patient's airway remains unobstructed.

Neonates and infants undergo a myriad of procedures under deep sedation. Oftentimes, a pacifier is used to help to alleviate the baby's discomfort during the procedure. However, it has been found that it can be difficult to monitor end tidal $CO_2$ ($ETCO_2$) when a pacifier is being utilized to alleviate the baby's discomfort during these procedures. Therefore, a clinician must choose between using a hard oral airway to ensure that the baby's airway remains unobstructed, or a pacifier to comfort the baby—both a hard oral airway and a pacifier cannot currently be used simultaneously.

Thus, there is a need for a new and improved apparatus that simultaneously (i) maintains an open fluidic pathway for respiratory gasses to be passed and thereafter analyzed, and (ii) permits a pacifier to be placed in a patient's mouth to provide the comforting aspects of the pacifier during a procedure.

SUMMARY OF THE INVENTION

The present invention comprises the provision and use of a new and improved apparatus that simultaneously (i) maintains an open fluidic pathway for respiratory gasses to be passed and thereafter analyzed, (ii) permits a pacifier to be placed in a patient's mouth to provide the comforting aspects of the pacifier during a procedure.

More particularly, the present invention comprises novel apparatus and methods which combines the ability to monitor end tidal carbon dioxide ($ETCO_2$), relieve airway obstruction, and use of a pacifier by the patient. To this end, the present invention comprises the provision and use of a novel pacifier comprising a passthrough (e.g., an opening), and an attachment for attaching tubing to the pacifier which carries gas samples from the patient's exhalation breath to the anesthesia machine for gas analysis.

In one preferred form of the present invention, there is provided apparatus for passing exhaled gasses from a mouth of a patient to a gas analyzer, the apparatus comprising:

- a pacifier comprising a distal end, a proximal end and an opening extending from the distal end to the proximal end, wherein the distal end comprises a nipple configured to be inserted into the mouth of the patient and the proximal end comprises a base configured to be positioned against the mouth of the patient; and
- a connector for connecting the pacifier to the gas analyzer.

In another preferred form of the present invention, there is provided a method for passing exhaled gasses from a mouth of a patient to a gas analyzer, the method comprising:

- providing apparatus comprising:
  - a pacifier comprising a distal end, a proximal end and an opening extending from the distal end to the proximal end, wherein the distal end comprises a nipple configured to be inserted into the mouth of the patient and the proximal end comprises a base configured to be positioned against the mouth of the patient; and
  - a connector for connecting the pacifier to the gas analyzer;
- disposing the distal end of the pacifier in the mouth of the patient; and
- passing fluid from the mouth of the patient through the opening formed in the pacifier to the gas analyzer.

In another preferred form of the present invention, there is provided apparatus for passing exhaled gasses from a patient to a gas analyzer, the apparatus comprising:

a pacifier comprising a distal end and a proximal end, wherein the distal end comprises a nipple configured to be inserted into the mouth of the patient; and tubing for passing exhaled gasses from the patient to the gas analyzer;

wherein the pacifier comprises a connector for connecting the tubing to the pacifier.

BRIEF DESCRIPTION OF THE DRAWINGS

These and other objects and features of the present invention will be more fully disclosed or rendered obvious by the following detailed description of the present invention, which is to be considered together with the accompanying drawings wherein like numbers refer to like parts and further wherein.

DETAILED DESCRIPTION OF THE PREFERRED EMBODIMENTS

The present invention comprises the provision and use of a new and improved apparatus that simultaneously (i) maintains an open fluidic pathway for fluid (e.g., respiratory gasses) to be passed and thereafter analyzed, and (ii) permits a pacifier to be placed in a patient's mouth to provide the comforting aspects of the pacifier during a procedure.

Figure 1:
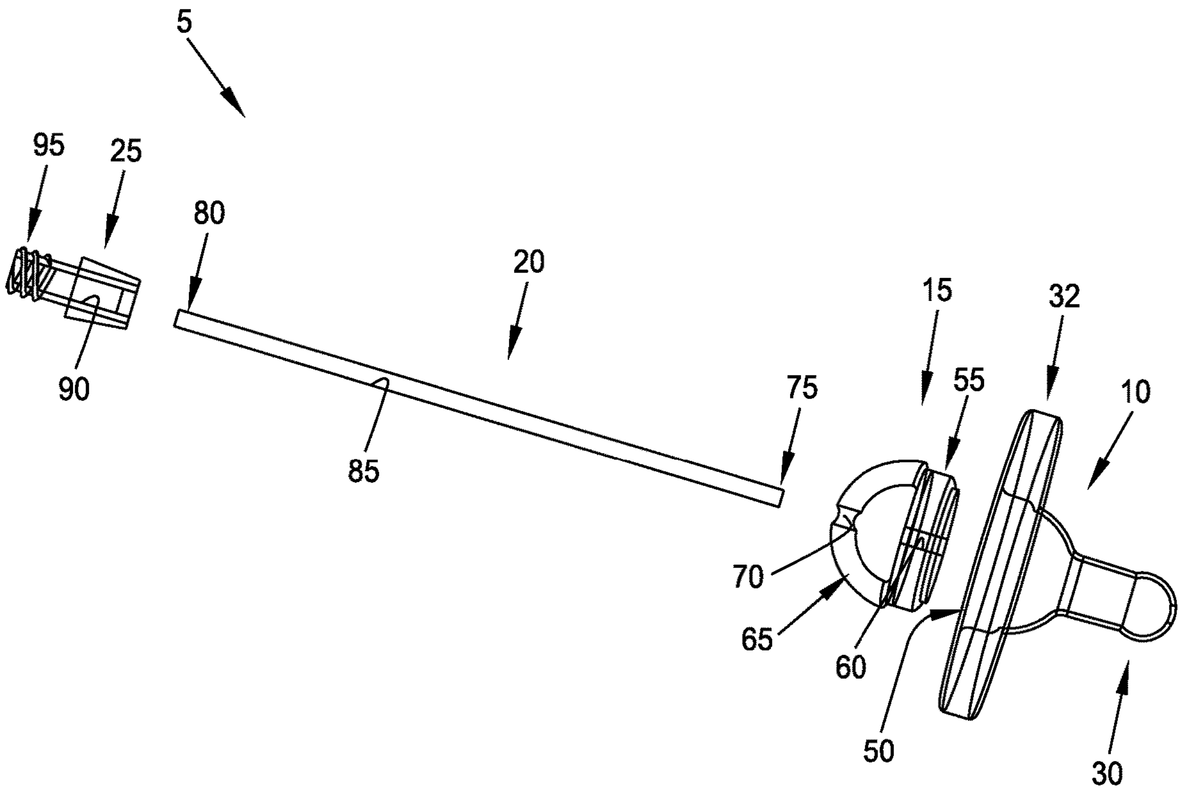
FIG. 1 is an exploded isometric view of a novel apparatus formed in accordance with the present invention.
Figure 2:
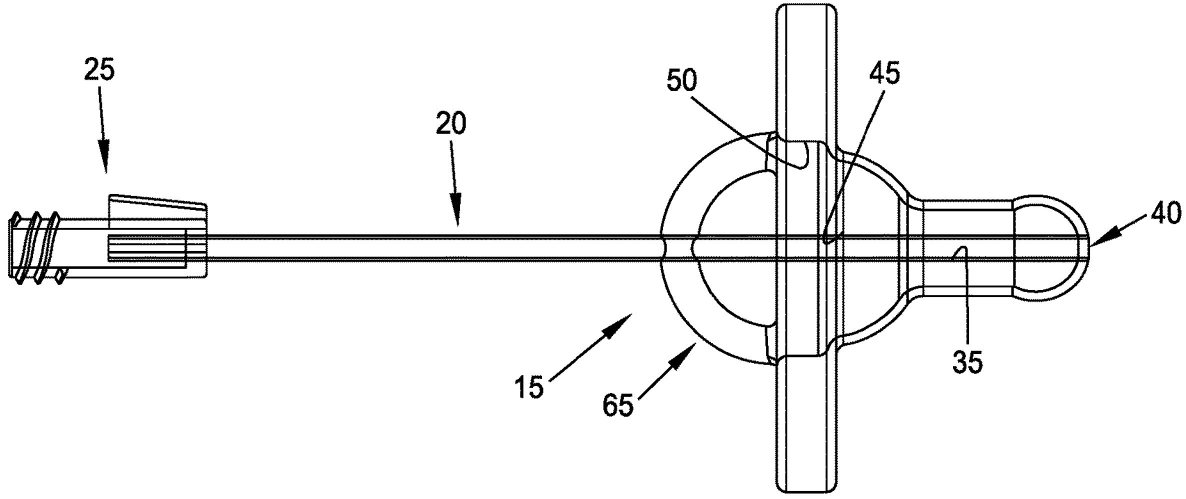
FIG. 2 is a side view of the apparatus of FIG. 1, showing further aspects of the invention.
Figure 3:
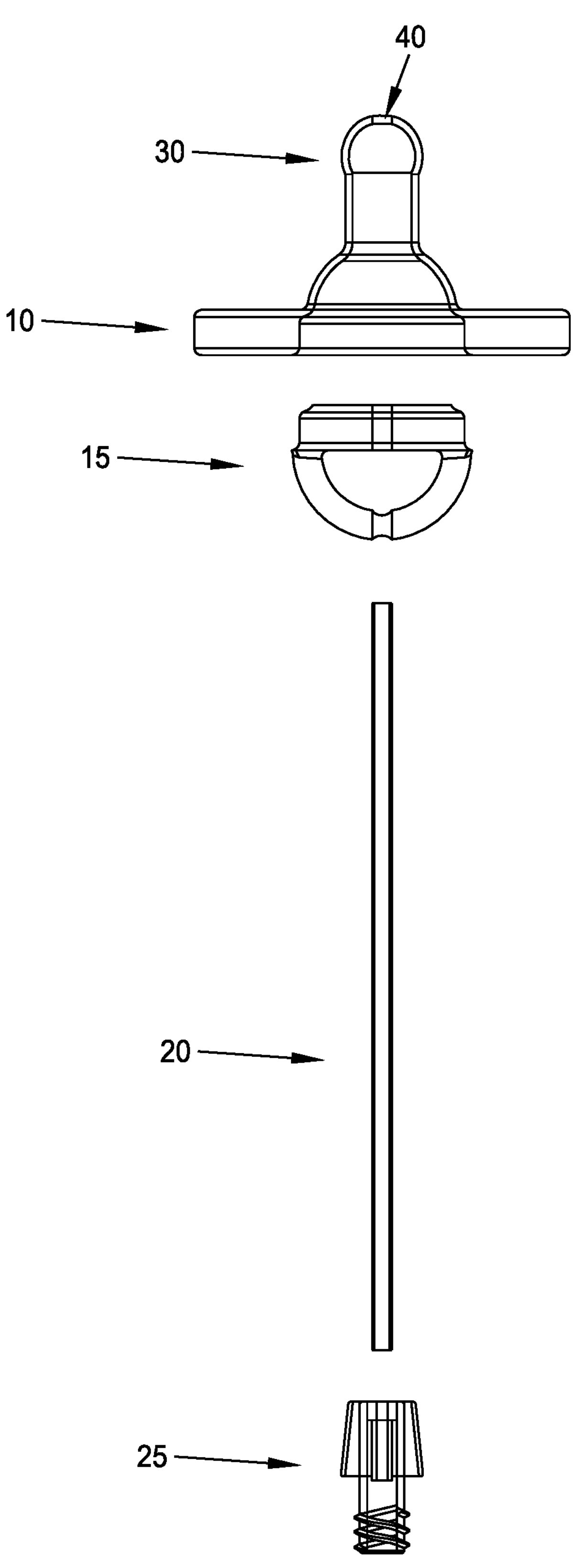
FIGS. 3-11 are schematic views of the apparatus of FIG. 1 showing further aspects of the invention.
Figure 4:
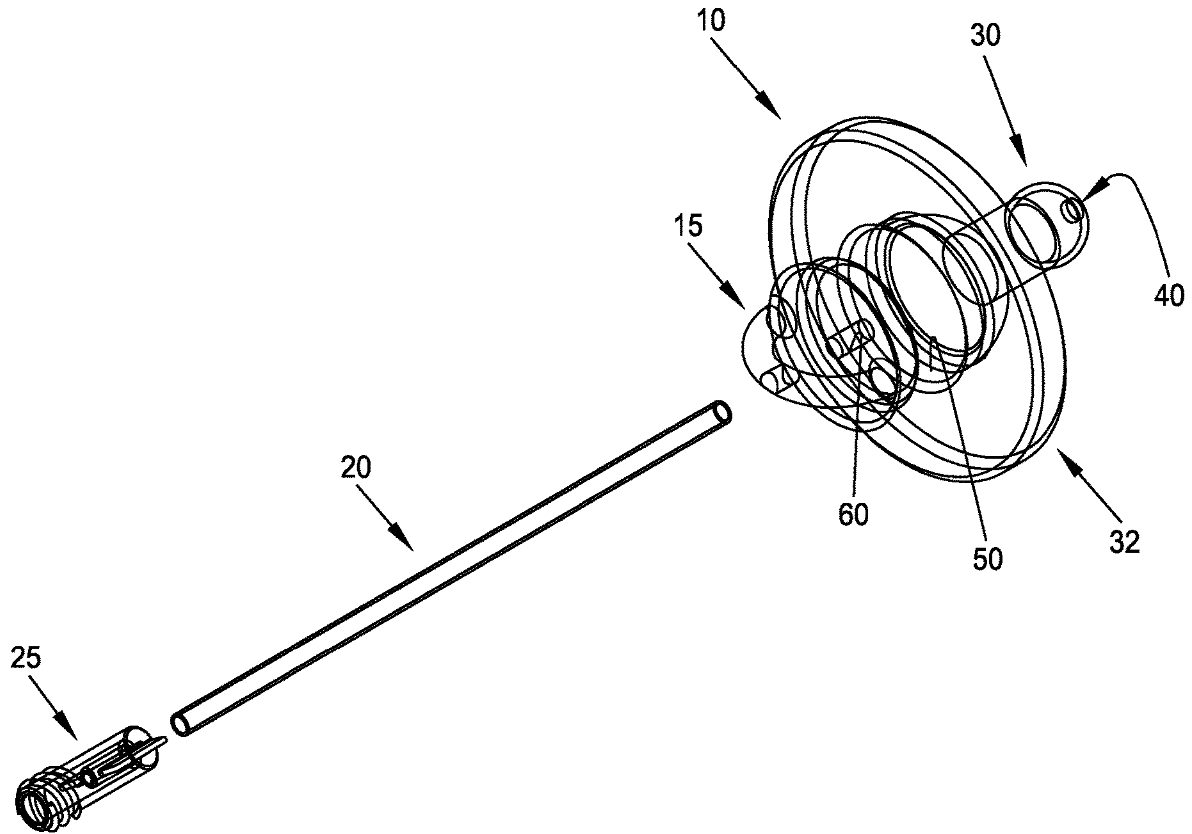
Figure 5:
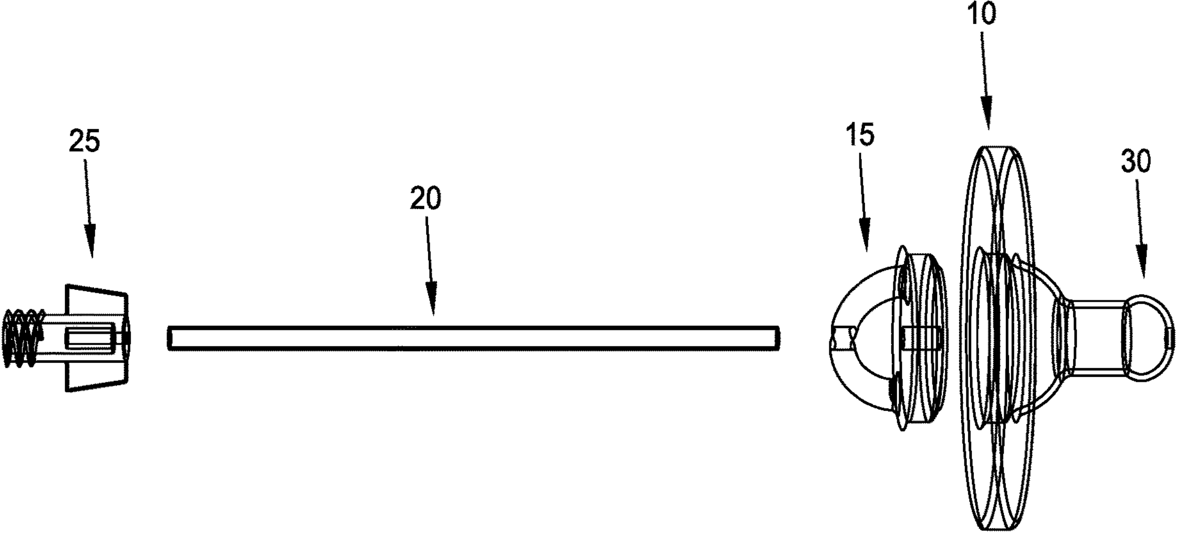
Figure 6:
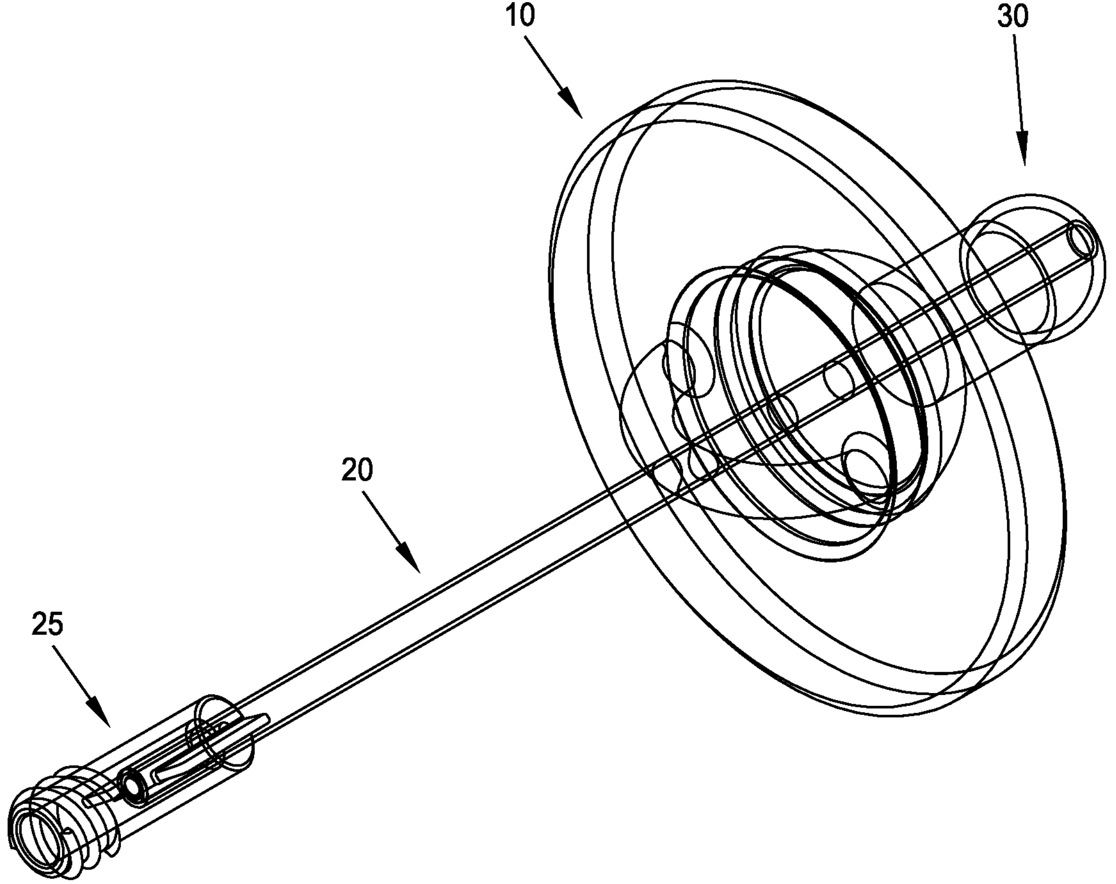
Figure 7:
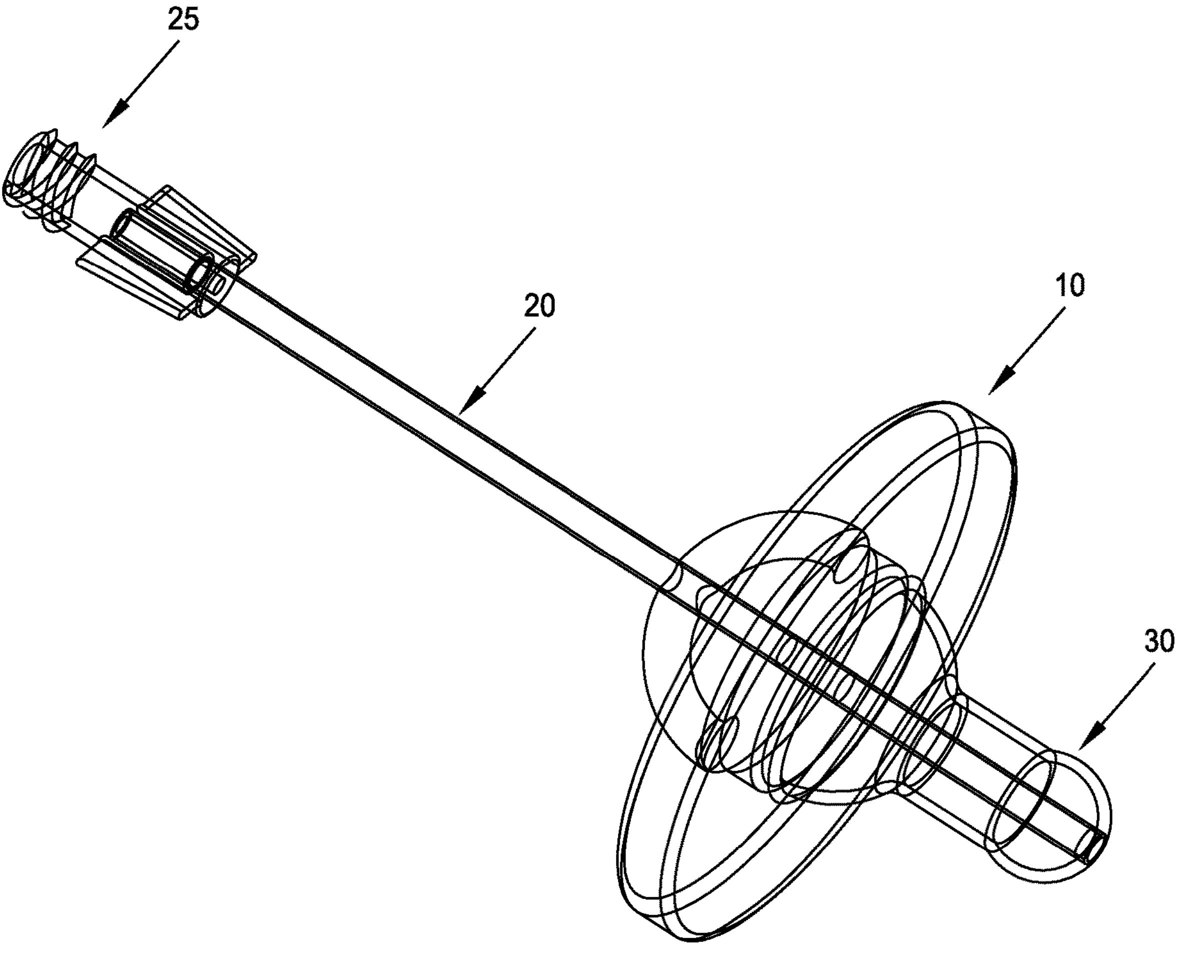
Figure 8:
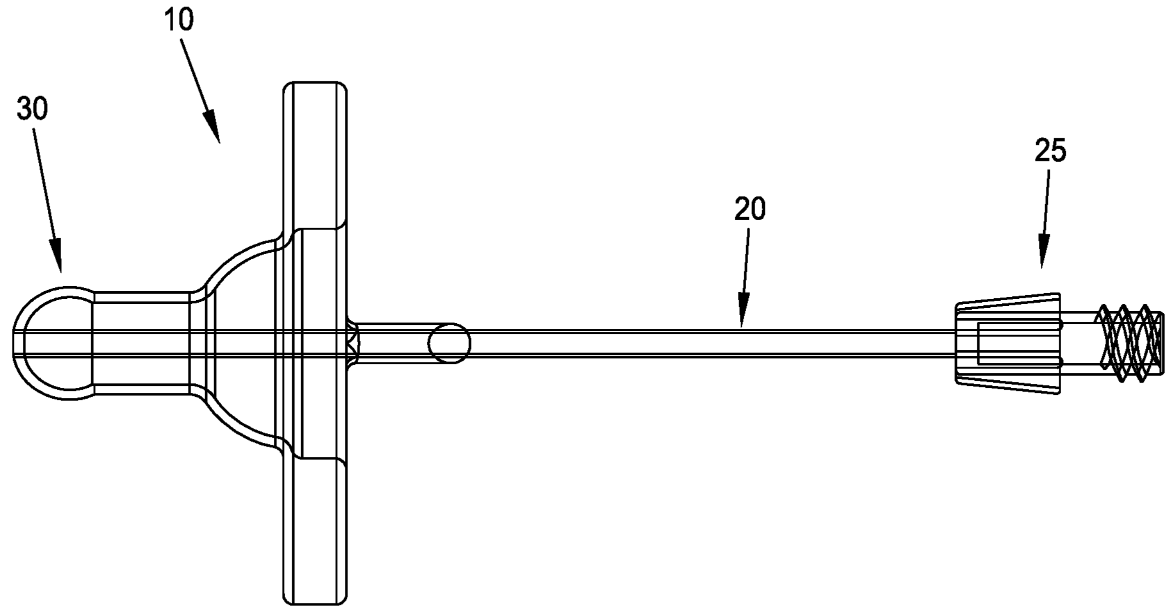
Figure 9:
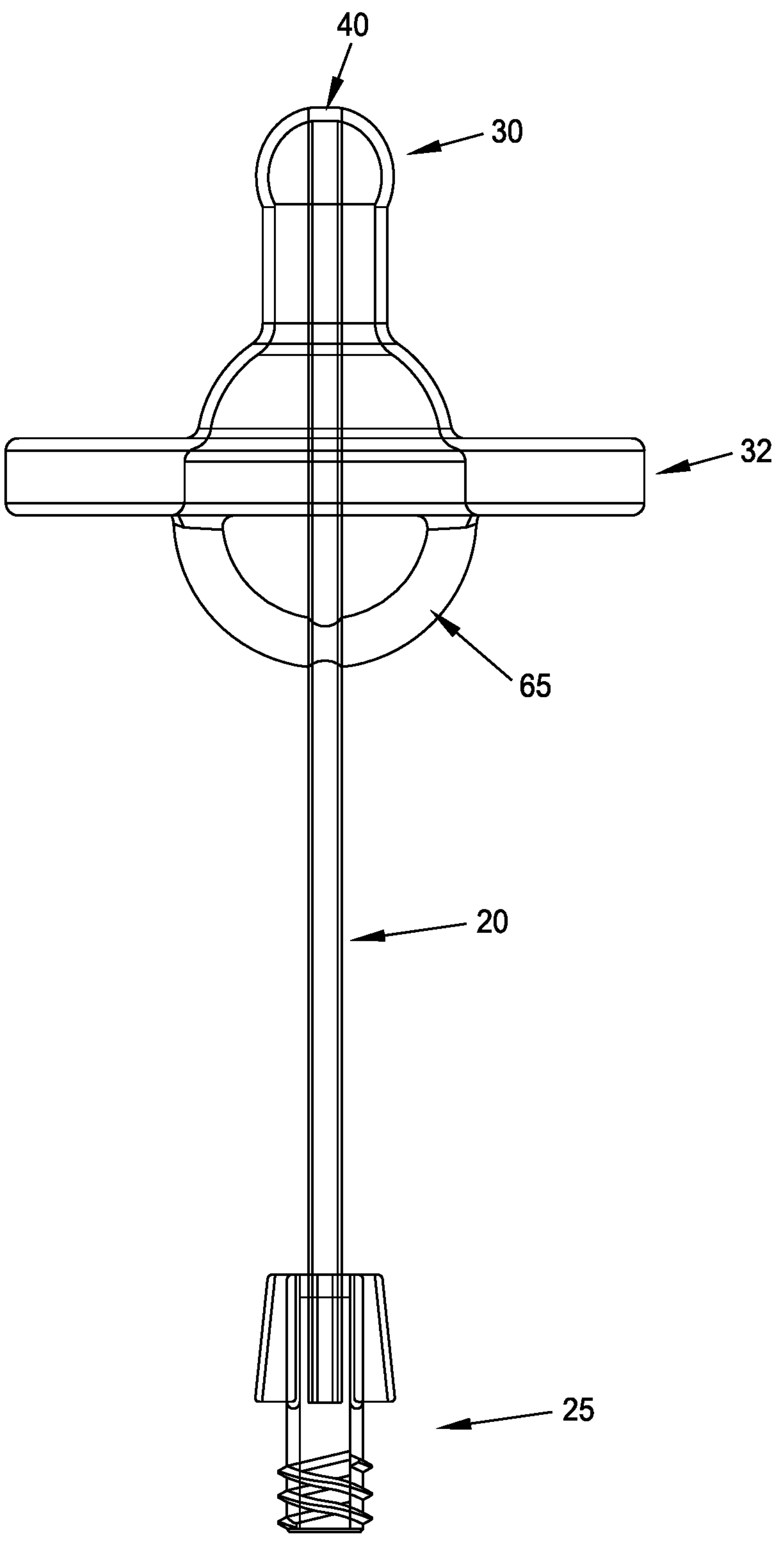
Figure 10:
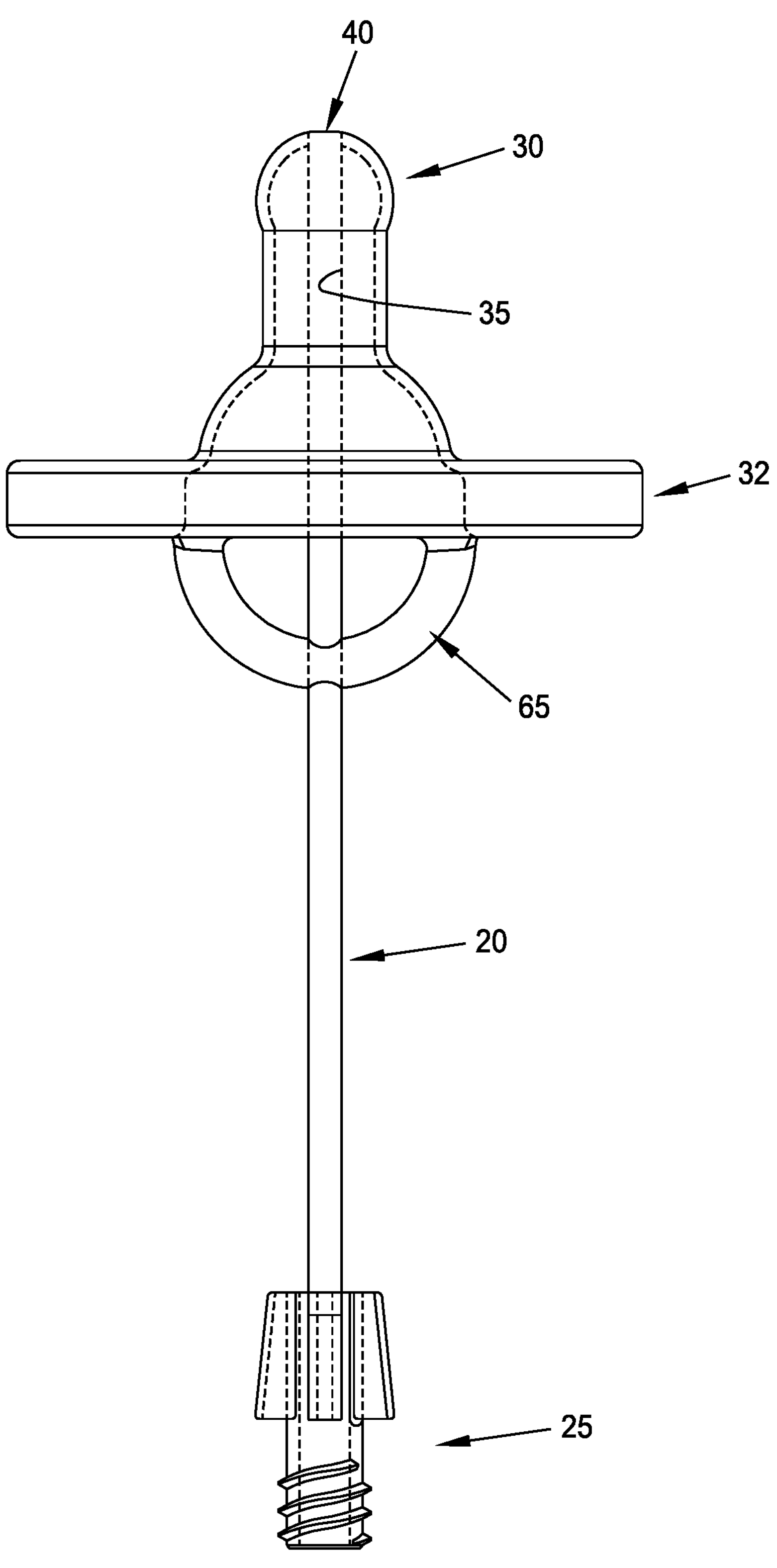
Figure 11:
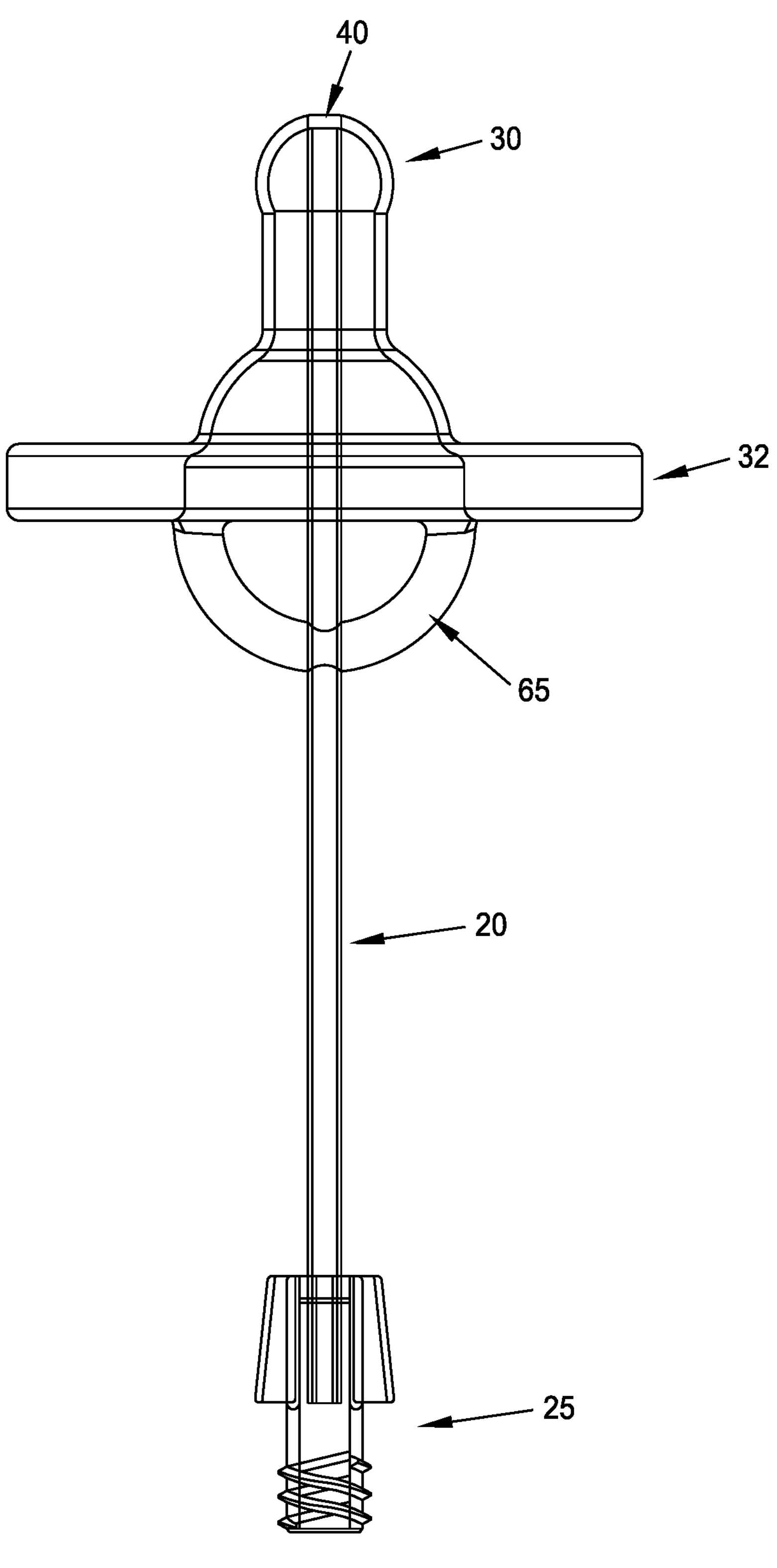

More particularly, and looking now at FIGS. 1 and 2, there is shown a novel gas exchange monitoring system 5 formed in accordance with the present invention. Gas exchange monitoring system 5 generally comprises a pacifier 10, a strain relief component 15, tubing 20 mounted to base pacifier 10 and a connector 25 for connecting an end of tubing 20 to a gas analyzer (not shown).

Pacifier 10 is configured to be inserted directly into, and retained in, the patient's mouth. To this end, pacifier 10 preferably comprises a nipple 30 for disposition within the mouth of the patient, and a base 32 for lodging against the lips of the patient. A central opening 35 is formed in nipple 30 and base 32 so as to pass centrally through pacifier 10. Central opening 35 comprises a distal opening 40 opening near the central apex of nipple 30 and a proximal opening 45 (see FIG. 2) opening onto a proximal seat 50 formed in pacifier 10.

Strain relief component 15 supports tubing 20 and prevents tubing 20 from kinking, which would otherwise obstruct the flow of exhalation gases from the infant patient's mouth to the gas analyzer.

In a preferred form of the present invention, strain relief component 15 comprises a base 55 sized to be received in proximal seat 50 of pacifier 10, whereby to releasably mount strain relief component 15 to pacifier 10 (e.g., via an interference fit and/or adhesive and/or welding).

Base 55 of strain relief component 15 comprises a central opening 60 sized to receive tubing 20 therein, as will hereinafter be discussed in further detail. It will be appreciated that central opening 60 of base 55 is sized and configured to be aligned with proximal opening 45 of central opening 35 of pacifier 10 when base 55 is mounted in proximal seat 50 of pacifier 10, whereby to fluidically connect central opening 60 of base 55 with central opening 35 of pacifier 10. A proximally-extending support arch 65 is mounted to base 55 of strain relief component 15 and extends proximally therefrom. Support arch 65 is preferably mounted to base 55 so as to be just outside of a central axis of base 55, whereby to be disposed alongside tubing 20 when tubing 20 is mounted to central opening 60 of base 55, as will hereinafter be discussed in further detail. Support arch 65 preferably comprises a scalloped cutout 70 formed at approximately the apex of support arch 65, with scalloped cutout 70 comprising a geometry selected to match that of tubing 20 when tubing 20 is mounted to central opening 60 of base 55, as will hereinafter be discussed in further detail.

Tubing 20 generally comprises an open distal end 75, an open proximal end 80, and a lumen 85 extending therebetween. Tubing 20 is preferably mounted to pacifier 10 by inserting distal end 75 of tubing 20 into central opening 60 of base 55 of strain relief component 15 such that distal end 75 of tubing 20 is retained within central opening 60 (e.g., via an interference fit and/or adhesive, via welding, etc.).

Alternatively, if desired, distal end 75 of tubing 20 may be passed through central opening 60 and into (or through) central opening 35, whereby to mount distal end 75 of tubing 20 intermediate central opening 35 (e.g., via an interference fit and/or adhesive, via welding, etc.).

Alternatively, if desired, distal end 75 of tubing 20 may pass entirely through both central opening 60 of base 55 and central opening 35 of pacifier 10 such that distal end 75 passes out of distal opening 40 of nipple 30, such that distal end 75 may reside directly in the patient's mouth when pacifier 10 is inserted into the patient's mouth.

Proximal end 80 of tubing 20 is mounted to one end of a central lumen 90 passing through connector 25. A connection element 95 (e.g., one half of a luer lock connector) is disposed on the proximal end of connector 25 for connecting the proximal end of connector 25 to a gas analyzer (not shown).

Thus it will be appreciated that gas exchange monitoring system 5 is configured to interface with (i.e., fluidically connect to) gas analysis equipment (not shown). As a result of the construction discussed above, when strain relief component 15 is mounted to pacifier 10 and tubing 20 is mounted to pacifier 10 (e.g., via mounting distal end 75 of tubing 20 to central opening 60 of base 55, via mounting distal end 75 of tubing 20 to central opening 35 of pacifier 10, etc.), connector 25 is fluidically connected to distal opening 40 of nipple 30, and hence gasses may be passed from the patient's mouth, into distal opening 40 of nipple 30, and through tubing 20 to a gas analyzer (e.g., a gas analyzer configured to determine the concentration of $CO_2$ present in a gas sample) mounted to connection element 95 of connector 25, without requiring the patient to remove pacifier 10 from their mouth.

Thus, it will be seen that gas exchange monitoring system 5 of the present invention facilitates measurement of the concentration of $CO_2$ in an infant patient's exhalation breath (in order to analyze and monitor how well an infant patient's circulation and gas exchange system is performing during a medical procedure) while also permitting the infant patient to retain a pacifier in its mouth during the medical procedure (thereby providing comfort to the infant patient during the medical procedure).

Thus, it will be seen that the present invention provides an improved method and apparatus for measuring the concentration of $CO_2$ in an infant patient's exhalations during a medical procedure (e.g., an exam, a surgical procedure, etc.) in order to gauge how well an infant patient's circulation and gas exchange system is performing while simultaneously (i) preventing the infant patient's airway from being obstructed, and (ii) soothing the infant patient's discomfort.

Alternative Pacifier 10A Comprising a Connector for Direct Connection to Gas Analyzer It should also be appreciated that, if desired, tubing 20 may be omitted, and pacifier 10A may comprise a connector 100 (e.g., a Luer lock) mounted directly to pacifier 10.

Figure 12:
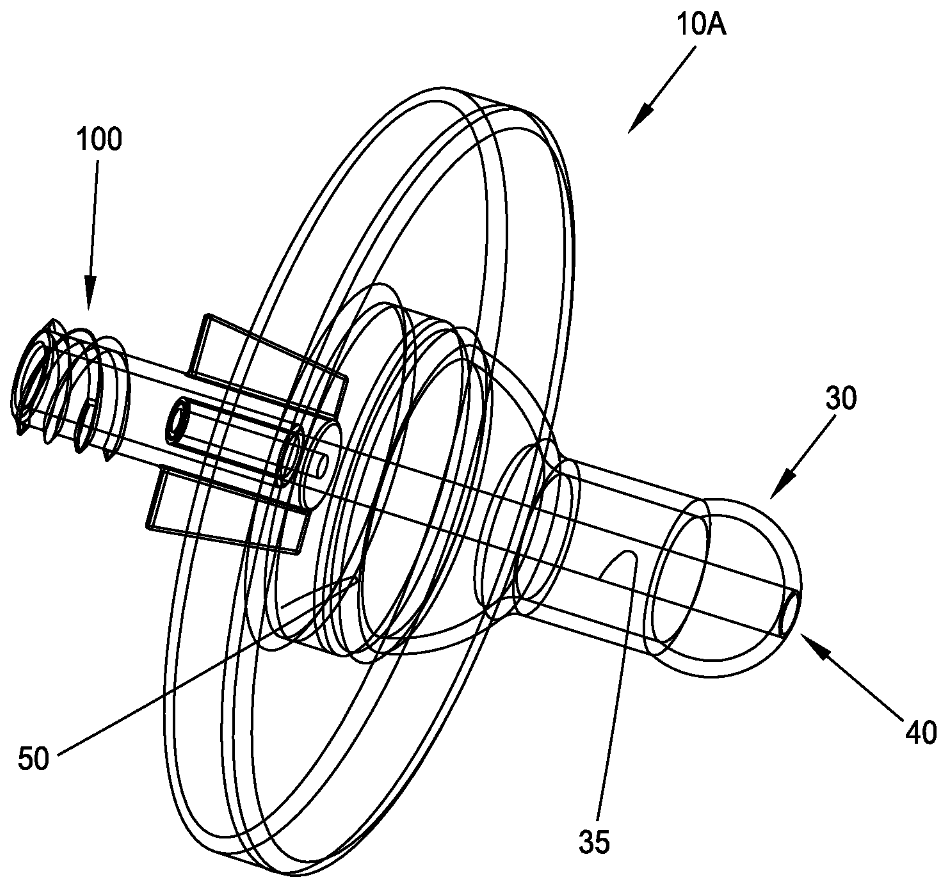
FIG. 12 is a schematic view showing an alternative form of the present invention.
Figure 13:
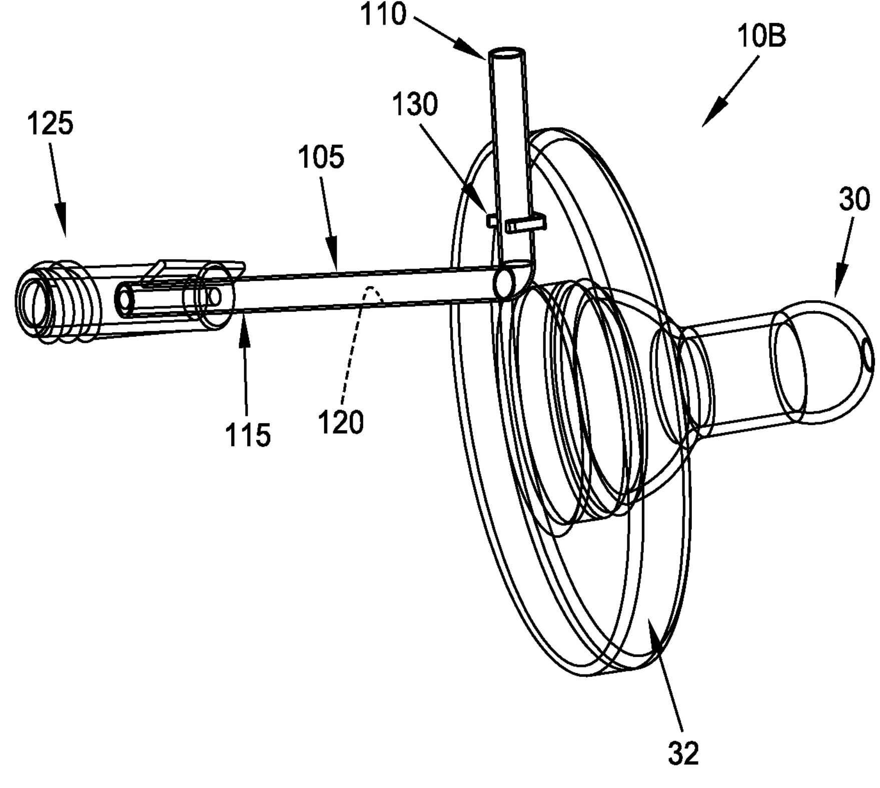
FIGS. 13-17 are schematic views showing another alternative form of the present invention.
Figure 14:
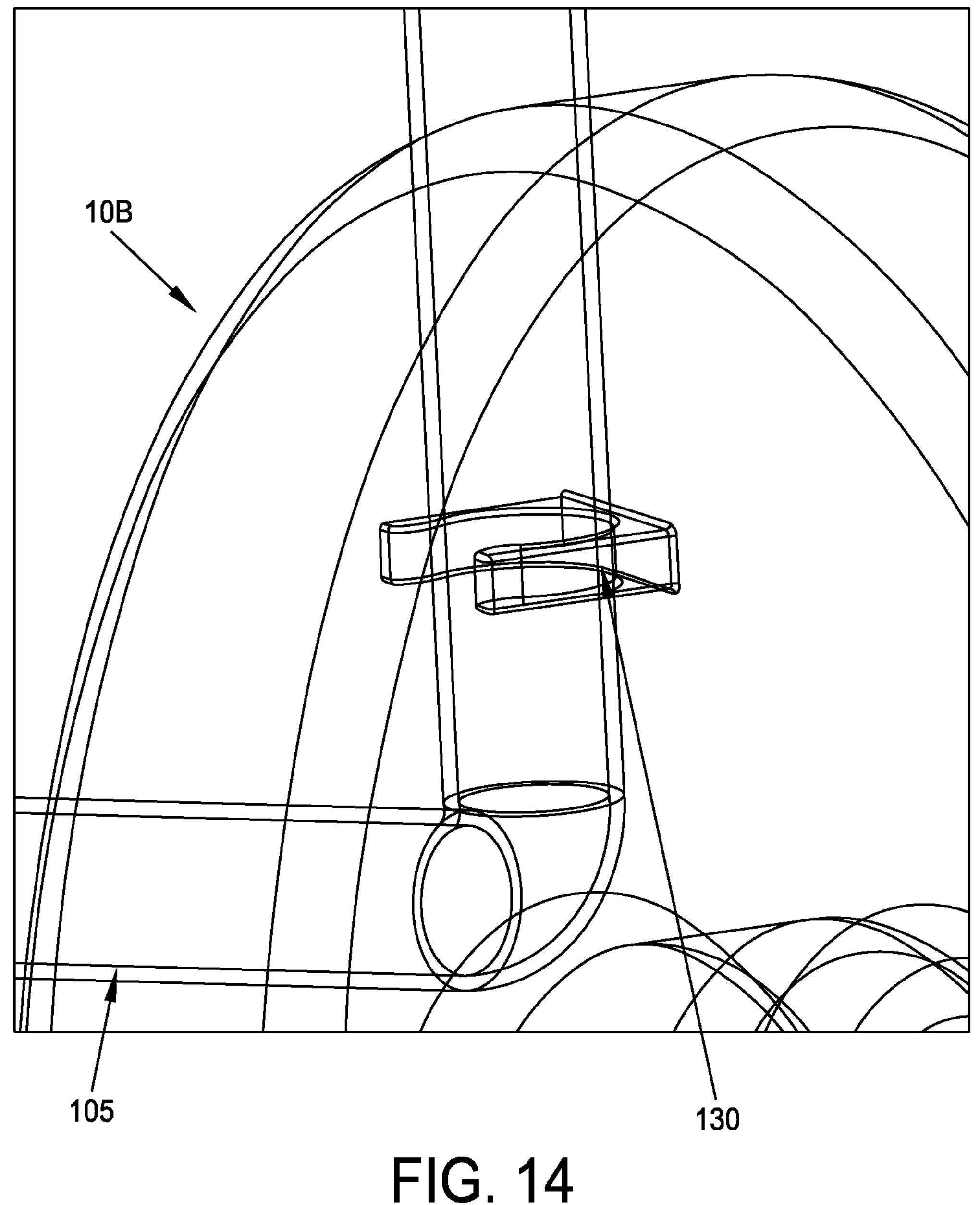
Figure 15:
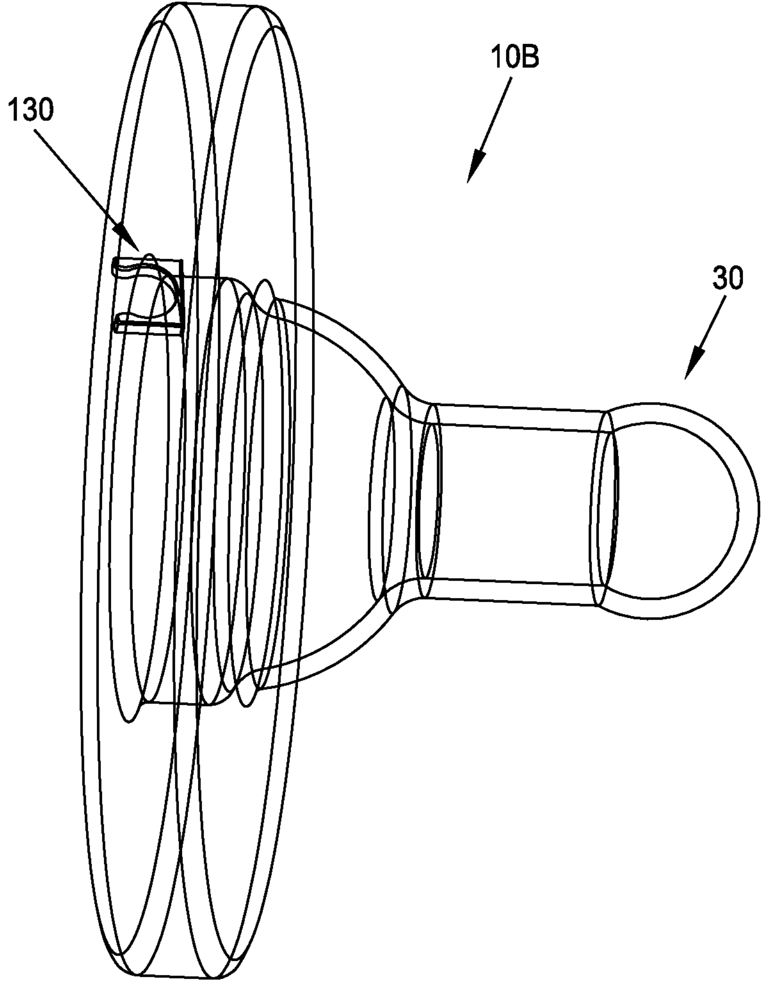
Figure 16:
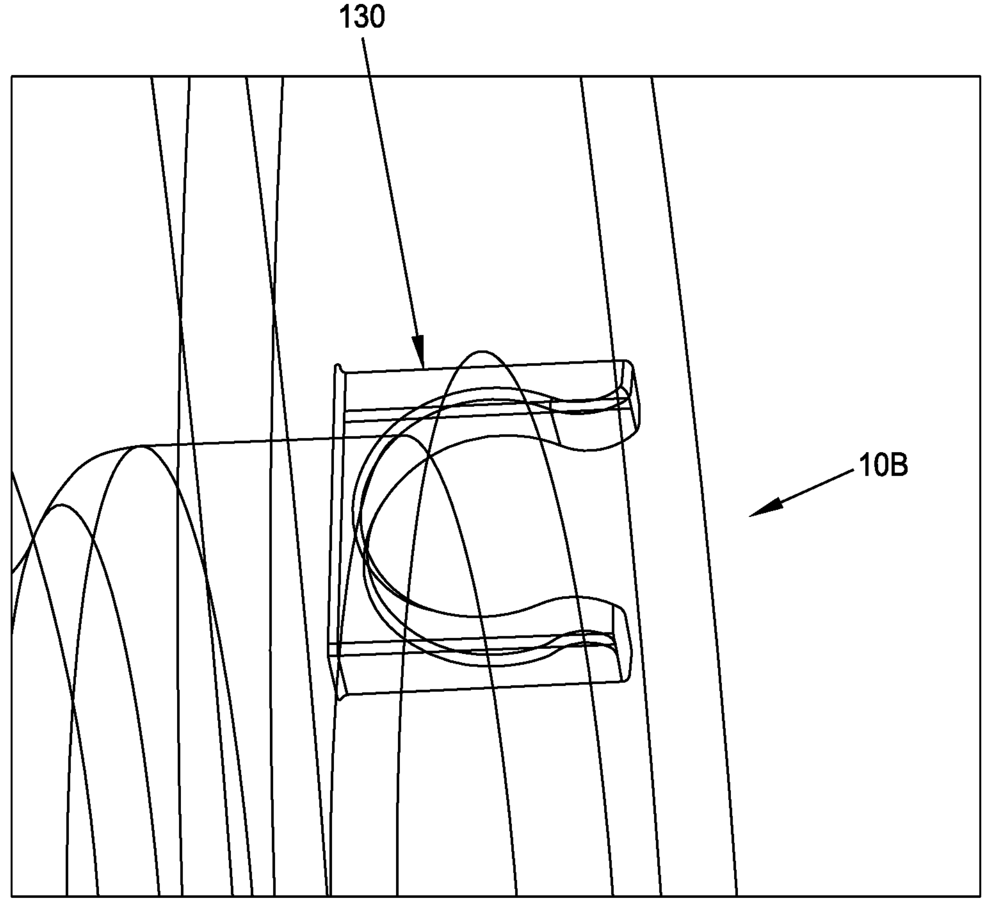
Figure 17:
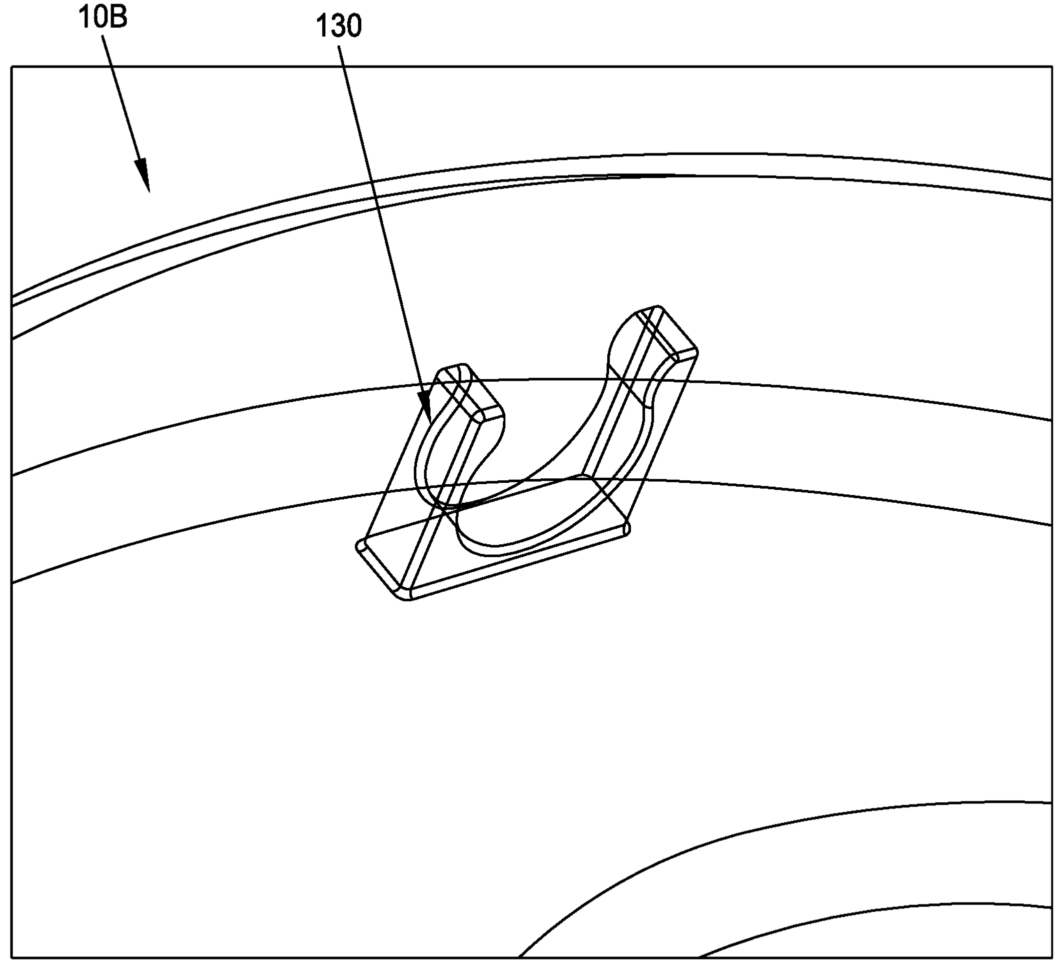

More particularly, and looking now at FIG. 12, with this form of the invention, the gas analyzer is connected directly to connector 100 mounted to a proximal side of pacifier 10A. By way of example but not limitation, if desired, connector 100 may mount to pacifier 10A in proximal seat 50 in lieu of strain relief component 15.

In use, with this form of the invention, the infant patient's exhaled gasses (i.e., exhaled breath) are passed through distal opening 40 of nipple 30 of pacifier 10A, into central opening 35, through connector 100 and into an appropriate gas analyzer connected to connector 100, whereby to permit the infant patient's exhaled gasses (e.g., exhaled breath) to be monitored by the gas analyzer in order to calculate the patient's $ETCO_2$.

Alternative Pacifier 10B Comprising a Clip for Attaching Tubing to the Pacifier It should also be appreciated that, if desired, tubing may be directly connected to the infant patient's nasal cavity (instead of passing the tubing through an opening in the pacifier), permitting $ETCO_2$ to be monitored by external equipment, and a mechanism may be used to attach the tubing to the pacifier so that the pacifier may still be placed in a patient's mouth to provide the comforting aspects of a pacifier during a procedure.

More particularly, one or more tubes may be mounted to a pacifier such that one end of the tube is in fluid communication the infant patient's nasal cavity, and the other end is fluidically connected to an appropriate gas analyzer (e.g., via a luer lock connector). The tubes may be used in place of, or in addition to, the aforementioned pacifiers 10 and 10A.

Looking now at FIGS. 13-17, in this form of the invention, there is provided a tube 105 comprising a distal end 110, a proximal end 115, and a lumen 120 extending therebetween. In a preferred form of the invention, a connector 125 (e.g., a luer lock connector) is mounted to proximal end 115 of tube 105, whereby to fluidically connect an appropriate gas analyzer (not shown) to lumen 120, as will be appreciated by one of skill in the art in view of the present disclosure.

A clip 130 is mounted to (or formed integral with) base 32 of pacifier 10B, whereby to secure tube 105 to pacifier 10B such that distal end 110 of tube 105 will be presented to the nasal cavity of the infant patient when nipple 30 of pacifier 10B is disposed in the mouth of the infant patient. Clip 130 is preferably sized to retain tube 105 via an interference fit (e.g., a "snap" fit) such that tube 105 is releasably attached to pacifier 10B.

In use, with this form of the invention, the infant patient's exhaled gasses (i.e., exhaled breath) are passed through distal end 110 of tube 105, through lumen 120 of tube 105, through connector 125 and into an appropriate gas analyzer connected to connector 125, whereby to permit the infant patient's exhaled gasses (e.g., exhaled breath) to be monitored by the gas analyzer in order to calculate the patient's $ETCO_2$.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. Apparatus for passing exhaled gasses from a mouth of a patient to a gas analyzer, the apparatus comprising:

a pacifier comprising a distal end, a proximal end and an opening extending from the distal end to the proximal end, wherein the distal end comprises a nipple configured to be inserted into the mouth of the patient and the proximal end comprises a base configured to be positioned against the mouth of the patient;

a strain relief component comprising a base mounted to the base of the pacifier, a support arch, a first opening in the base of the strain relief component, and a second opening in the support arch;

a tube comprising a distal end, a proximal end and a lumen extending between the distal end of the tube and the proximal end of the tube, wherein the distal end of the tube is mounted to the base of the strain relief component, and further wherein the tube extends through the first opening of the base of the strain relief component and through the second opening of the support arch of the strain relief component; and a connector mounted to the proximal end of the tube for fluidically connecting the pacifier to the gas analyzer.

2. The apparatus of claim 1 wherein the connector is a luer lock connector.

3. The apparatus of claim 1 wherein the gas analyzer determines the end tidal $CO_2$ of the patient.

4. The apparatus of claim 1 wherein the strain relief component is mounted to the pacifier via an interference fit between the base of the pacifier and the base of the strain relief component.

5. A method for passing exhaled gasses from a mouth of a patient to a gas analyzer, the method comprising:

providing apparatus comprising:

a pacifier comprising a distal end, a proximal end and an opening extending from the distal end to the proximal end, wherein the distal end comprises a nipple configured to be inserted into the mouth of the patient and the proximal end comprises a base configured to be positioned against the mouth of the patient;

a strain relief component comprising a base mounted to the base of the pacifier, a support arch, a first opening in the base of the strain relief component, and a second opening in the support arch;

a tube comprising a distal end, a proximal end and a lumen extending between the distal end of the tube and the proximal end of the tube, wherein the distal end of the tube is mounted to the base of the strain relief component, and further wherein the tube extends through the first opening of the base of the strain relief component and through the second opening of the support arch of the strain relief component; and a connector mounted to the proximal end of the tube for fluidically for connecting the pacifier to the gas analyzer;

disposing the distal end of the pacifier in the mouth of the patient; and passing fluid from the mouth of the patient through the opening formed in the pacifier, through the tube to the gas analyzer.

6. The method of claim 5 further comprising analyzing the fluid passed from the mouth of the patient to determine the end tidal $CO_2$ of the patient.

7. The method of claim 5 wherein the connector is a luer lock connector.

8. The method of claim 5 wherein the strain relief component is mounted to the pacifier via an interference fit between the base of the pacifier and the base of the strain relief component.

* * * * *